United States Patent [19]

Tusa et al.

[11] Patent Number: 5,134,998

[45] Date of Patent: Aug. 4, 1992

[54] SYSTEM AND METHOD FOR PREDICTING THE VALUE OF A COMPOSITIONAL PARAMETER OF BLOOD

[75] Inventors: James K. Tusa, Carlsbad; William W. Miller, Santa Ana, both of Calif.

[73] Assignee: Minnesota Mining and Manufacturing Company, St. Paul, Minn.

[21] Appl. No.: 514,703

[22] Filed: Apr. 26, 1990

[51] Int. Cl.$^5$ ............................................. A61B 5/00
[52] U.S. Cl. ................................. 128/632; 128/637; 436/68; 364/413.09
[58] Field of Search ............... 128/632, 633, 637, 748, 128/760, 771; 210/645; 364/922.2, 922.3, 413.09; 422/80, 81; 436/68

[56] References Cited

U.S. PATENT DOCUMENTS

| | | | |
|---|---|---|---|
| 3,720,813 | 3/1973 | Badessa . | |
| 3,785,772 | 1/1974 | Coggeshall | 128/632 |
| 3,978,325 | 8/1976 | Goldstein et al. . | |
| 4,264,328 | 4/1981 | Marsoner | 436/68 |
| 4,649,928 | 3/1987 | Samaras et al. . | |
| 4,686,628 | 8/1987 | Lee et al. . | |
| 4,697,450 | 10/1987 | Bachman et al. | 128/633 |
| 4,727,500 | 2/1988 | Jackson et al. . | |
| 4,751,655 | 6/1988 | Peacock . | |
| 4,789,950 | 12/1988 | Saxe et al. . | |
| 4,954,318 | 9/1990 | Yafuso et al. | 128/634 |

FOREIGN PATENT DOCUMENTS 0336201 3/1989 European Pat. Off. .
0354736 8/1989 European Pat. Off. .

OTHER PUBLICATIONS

Matalon et al., "A Method for In Vitro Measurement of Tensions of Blood Gases with a Mass Spectrometer", Medical Instr. May 1975, pp. 133–135.

Wald et al, "Continuous Measurement of Blood Gases in Vivo by Mass Spectrography", Med. & Biol. Engng., Nov 17, 1969, pp. 111–128.

Marsoner, "Analogoue Electronic Oxygen-Saturation Calculator", Medical & Biol. Eng. & Comput, 1977, pp. 322–326.

Primary Examiner—Stephen C. Pellegrino
Assistant Examiner—Steven J. Shumaker
Attorney, Agent, or Firm—Gary L. Griswold; Walter N. Kirn; Dale E. Hulse

[57] ABSTRACT

A system for determining the value of a compositional parameter of blood, including a sensor for producing a signal related to the value of the compositional parameter. A computer analyzes the signal and produces an output representing the value of the compositional parameter of blood. There is a delayed response in the system such that the signal has a time-varying waveform that varies from an initial value to an equilibrated value. The equilibrated value is predicted by detecting the occurrence of an inflection point and then computing an estimate of the equilibrated value based upon the assumption that the waveform varies exponentially from the inflection point to the equilibrated value.

12 Claims, 7 Drawing Sheets

SYSTEM AND METHOD FOR PREDICTING THE VALUE OF A COMPOSITIONAL PARAMETER OF BLOOD

BACKGROUND OF THE INVENTION

It is often necessary or desirable to measure the value of various compositional parameters of blood, i.e., the presence and/or concentration of blood constituents, such as blood gases, hydrogen ions (pH), other electrolytes, glucose, red blood cells and the like. Measurements of the values of compositional parameters of blood can be accomplished electrochemically or optically using fluorescence or absorbance techniques.

Compositional parameters of blood can be monitored in real time using, for example, fluorescent sensors. The sensors occupy positions in a sensor housing or cassette adjacent a blood passageway. The sensors are illuminated with exciting light of one wavelength, and each of them emits a fluorescent emitted signal having an intensity which varies according to the value of the compositional parameter of blood to which the sensor responds. These signals are then processed to provide quantitative information concerning, or values of, the relevant compositional parameters.

After the sensors are exposed to the compositional parameters of blood, the signals emitted by the sensors change from some initial value to a final or equilibrated value over a length of time which may be minutes in duration. The resulting time delay can cause certain problems because the time passing before equilibration occurs may be significant in terms of blood coagulation time. Thus, there is a risk of coagulation in the cassette while waiting for the value to reach equilibrium.

SUMMARY OF THE INVENTION

This invention solves the problem outlined above by providing a system and method that predicts equilibrated values well ahead of their occurrence. The system of this invention determines the values of compositional parameters of blood quickly and conveniently, and it does so in a way that significantly reduces the time that the blood must contact the sensor. Accordingly, a blood sample drawn from a patient can be returned to the patient sooner, and the risk of clotting is correspondingly reduced.

Briefly, a system constructed according to the invention may include means for containing blood which may be means for drawing a blood sample, sensor means for producing a signal related to the value of the compositional parameter of blood, and computer means coupled to the sensor means for analyzing the signal and producing an output representing the value of the compositional parameter of blood.

The system has a delayed response. Thus, the signal produced by the sensor has a time-varying waveform $P(t)$ that varies from an initial value $P(t_0)$ occurring at a time $t_0$ at which the sensor is subjected to blood to an equilibrated value $P(t_E)$ occurring at a time $t_E$ thereafter.

The delayed response of the system a causes delay between the time that the sensor is subjected to blood at time $t_0$ and the time $t_E$ at which equilibration occurs. Although this delay may be caused by various factors, in one embodiment of the invention, one major factor is the physical barrier interposed between the blood and the indicator of the sensor. For example, the indicator may be a fluorescent indictor responsive to a blood gas of interest, and this indicator is physically separated from the blood by a semi-permeable barrier which is permeable to the blood gas of interest. The time required for the blood gas of interest or other compositional parameter to permeate the barrier and contact the indicator is one source of delay.

Another source of delay is the time required for the indicator to respond to the compositional parameter after the indicator is contacted by, or subjected to the action of, the compositional parameter of blood. Both of these delays are caused by the sensor itself. Although there may be other delays in the system, such as delays caused by the electronic equipment, generally these can be ignored. Accordingly, as a practical matter, the delay can be considered as introduced by the sensor.

The signal produced by the sensor deviates from an exponential function. According to a major aspect of the invention, the computer means includes means for detecting the occurrence of an inflection point $P(t_I)$ occurring between the initial value $P(t_0)$ and the equilibrated value $P(t_E)$ as well as means for computing an estimate of the equilibrated value $P(t_E)$ based upon the assumption that the waveform $P(t)$ varies exponentially from the inflection point $P(t_I)$ to the equilibrated value $P(t_E)$. Preferably, the means for computing an estimate of the equilibrated value $P(t_E)$ uses the relationship $$(A+B)_{est} = P(t_I) + [\text{Tau} * \text{MAX}(dp/dt)]$$

where $(A+B)_{est}$ is the estimate of the equilibrated value $P(t_E)$est, Tau is a constant describing the exponential time response after the inflection point, and $\text{MAX}(dp/dt)$ is the slope of $P(t)$ at the inflection point $P(t_I)$. For $CO_2$, an estimated value of Tau can be computed using the relationship $$\text{TAU}_{est} = K_1 + K_2/\text{MAX}(dp/dt)$$

where $\text{TAU}_{est}$ is the estimated value of Tau, $K_1$ is a first constant, $K_2$ is a second constant, and $\text{MAX}(dp/dt)$ is the slope of $P(t)$ at the inflection point $P(t_I)$. For the purposes of estimating Tau in the case of carbon dioxide, the value of $K_1$ is empirically determined to be 15 and that of $K_2$ is determined to be 5.5.

More generally, Tau can be estimated for virtually any compositional blood parameter using the relationship $$\text{TAU}_{est} = K_1 + K_2 * \text{MAX}(dp/dt)^{K_3} + K_4 * \text{MAX}(dp/pdt)^{K_5}$$

where $\text{MAX}(dp/dt)$ is the slope of $P(t)$ at the inflection point $P(t_1)$ and $\text{MAX}(dp/pdt)$ is the maximum value of the proportional slope of $P(t)$ occurring near the inflection point $P(t_I)$ and $K_1$, $K_2$, $K_3$, $K_4$ and $K_5$ are constants.

This invention may be used to project values of various compositional parameters of blood, including the partial pressure of oxygen, the partial pressure of carbon dioxide, pH value, glucose, red blood cells, various electrolytes, and the like. These values may be sensed in vivo, in vitro or in an extracorporeal loop. However, the invention is particularly adapted for projecting these values where there is some reason, such as patient safety and comfort, to accomplish the sensing task as rapidly as possible.

The sensor means may be optical, electrochemical or of any other type that produces a time-varying signal related to the value of a compositional parameter of blood. However, optical sensing provides certain advantages, and this invention is particularly adapted for use with fluorescent sensors.

DESCRIPTION OF THE PREFERRED EMBODIMENTS

Figure 1:
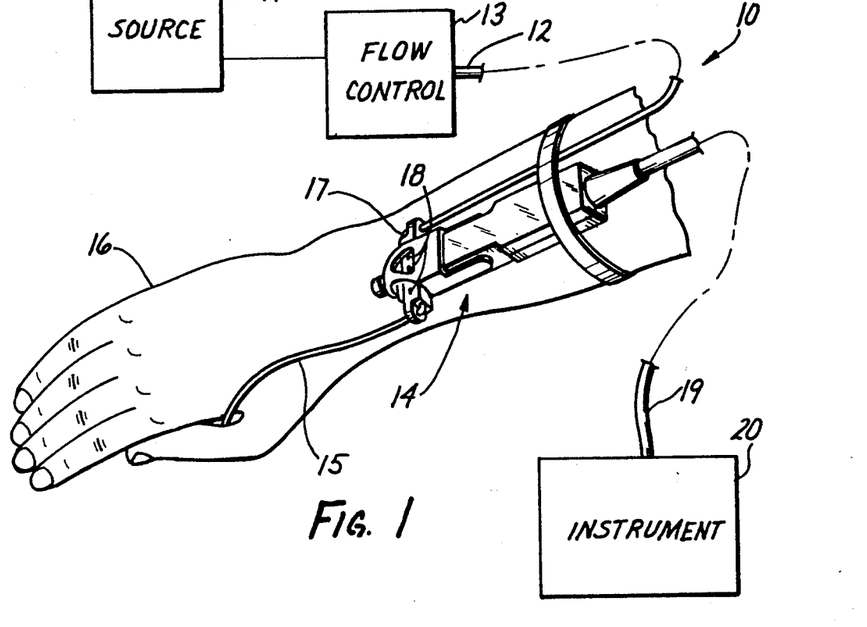
FIG. 1 of the drawings is a schematic representation of an assembly for measuring blood parameters of interest.

FIG. 1 illustrates an assembly 10 for measuring blood parameters of interest. Some principles of operation and the componentry employed are similar to those described in U.S. Pat. No. Re. 31,879 and copending U.S. application Ser. No. 229,617. Both those documents are incorporated by reference for the details of structure and operation provided.

Generally, the assembly 10 includes a source 11 of a flush solution, the flush solution flowing from the source 11 through a conduit 12 and various flow control components 13 toward a sensor assembly 14. The flush solution may be an anticlotting solution such as a heparinized saline solution, for example, and the flow control components may include such things as a volume oscillator in the form of a cylinder/piston type syringe that is capable of drawing a vacuum. Manual operation of the syringe draws a blood sample through a conduit 15 from a patient 16 into a disposable housing portion 17 of the sensor assembly 14 (FIG. 1). Thus, those components serve as means for drawing a blood sample.

After blood enters the housing portion 17, exciting light from an instrument 20 is transmitted along optical fibers of an optical fiber bundle 19 to three sensors 18 within the housing portion 17. In this embodiment, the sensors 18 respond to the partial pressure of oxygen, the partial pressure of $CO_2$ and the hydrogen ion concentration, respectively. Each of the sensors 18 produces a fluorescent-emitted signal of a different wavelength from the exciting light, and such emitted signals are related, respectively, to the blood compositional parameters to which they are responsive. These three emitted signals are transmitted to the instrument 20 over separate optical fibers or channels of the optical fiber bundle 19. The instrument 20 discriminates the emitted fluorescent signals from the exciting light.

Figure 1A:
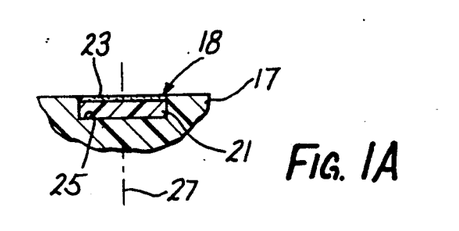
FIG. 1A is an enlarged, fragmentary, sectional view illustrating one form of sensor.

The details of one form of housing portion 17 and sensors 18 are shown by way of example in common assignee's application Ser. No. 229,617. FIG. 1A also shows by way of example one of the sensors 18. The sensor 18 includes a polymeric matrix 21 carrying a fluorescent indicator and a semi-permeable barrier in the form of an overcoat 23 which is permeable to the compositional parameter to be sensed. The matrix 21 and the overcoat 23 are carried in a cavity 25 of disposable housing portion 17. An optical fiber 27 conducts exciting light to the transparent housing portion 17 and hence to the indicator in the matrix 21 and also returns the fluorescent emitted signal to the instrument 20.

Many different embodiments of sensors may be used with this invention. However, it can be seen from FIG. 1A that it will take time for the compositional parameter of interest to permeate the semi-permeable barrier 23 and also the matrix 21 in order to contact the fluorescent indicator carried by the matrix. Once the compositional parameter has contacted the indicator in the matrix 21, additional time may be required for the indicator to react to the presence of the compositional parameter, and this is particularly true for carbon dioxide. Accordingly, predicting $P(t_E)$ for carbon dioxide is particularly important. For oxygen and pH, the reaction with the fluorescent indicator is rapid, and so the primary delay for oxygen is in crossing the barrier 23 and permeating the matrix 21.

Figure 2:
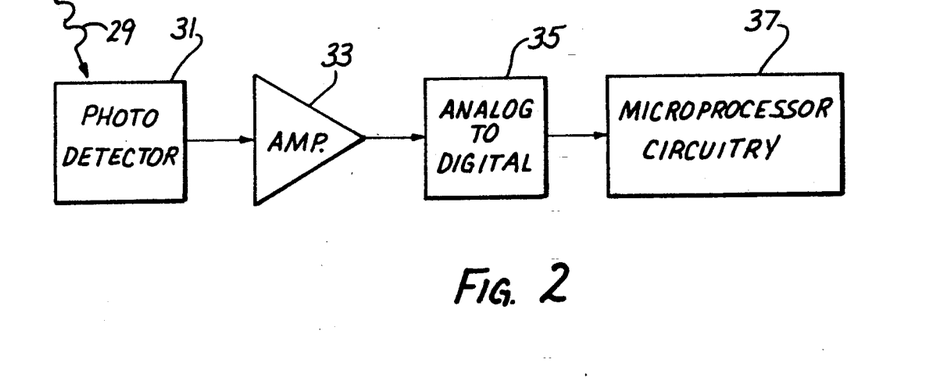
FIG. 2 is a block diagram of the components used in the instrument of FIG. 1.

One of the emitted fluorescent signals from one of the sensors is represented in FIG. 2 by an arrow 29. The instrument 20 includes the componentry necessary to extract information from the light signal 21. Thus, the instrument 20 includes a transducer, such as a photo detector 31, which serves as means to produce an electrical signal related to the light signal. In addition, it may include signal conditioning componentry, such as an amplifier 33 for amplifying the electrical signal, and an analog-to-digital converter 35 for producing digital data related to the electrical signal. The digital data is coupled by known means to microprocessor circuitry 37 that includes a microprocessor and suitable supporting hardware and software. Those things are configured in many ways according to known techniques so that the microprocessor can read and processes the digital data and then display or otherwise provide a readout of results. The microprocessor circuitry 37 may, for example, include a display and a keypad to facilitate communication with an operator, and it combines with the photo detector 31, the amplifier 33 and the analog-to-digital converter 35 to serve as computer means coupled to the sensor means for analyzing the signal and producing an output representing the value of the compositional parameters in the blood sample.

According to the present invention, the microprocessor circuitry 37 includes programming configured to predict final indicated values (i.e., equilibrated values) of certain compositional blood parameters. Doing so is important in order to reduce the time that blood must remain in the housing portion 17 and hence the likelihood of clotting.

The sensor assembly 14 has a delayed response such that the signal it produces has a time-varying waveform $P(t)$ that deviates from an exponential function as it varies from an initial value $P(t_0)$ occurring at a time $t_0$ at which the blood sample is drawn into the housing portion 17 and hence to the sensors 18 to an equilibrated value $P(t_E)$ occurring at a time $t_E$ thereafter. In that regard, $P(t)$ approaches the equilibrated value $P(t_E)$ asymptotically in the sense that it at least closely approximates the asymptotic approach of a true exponential function.

Figure 3:
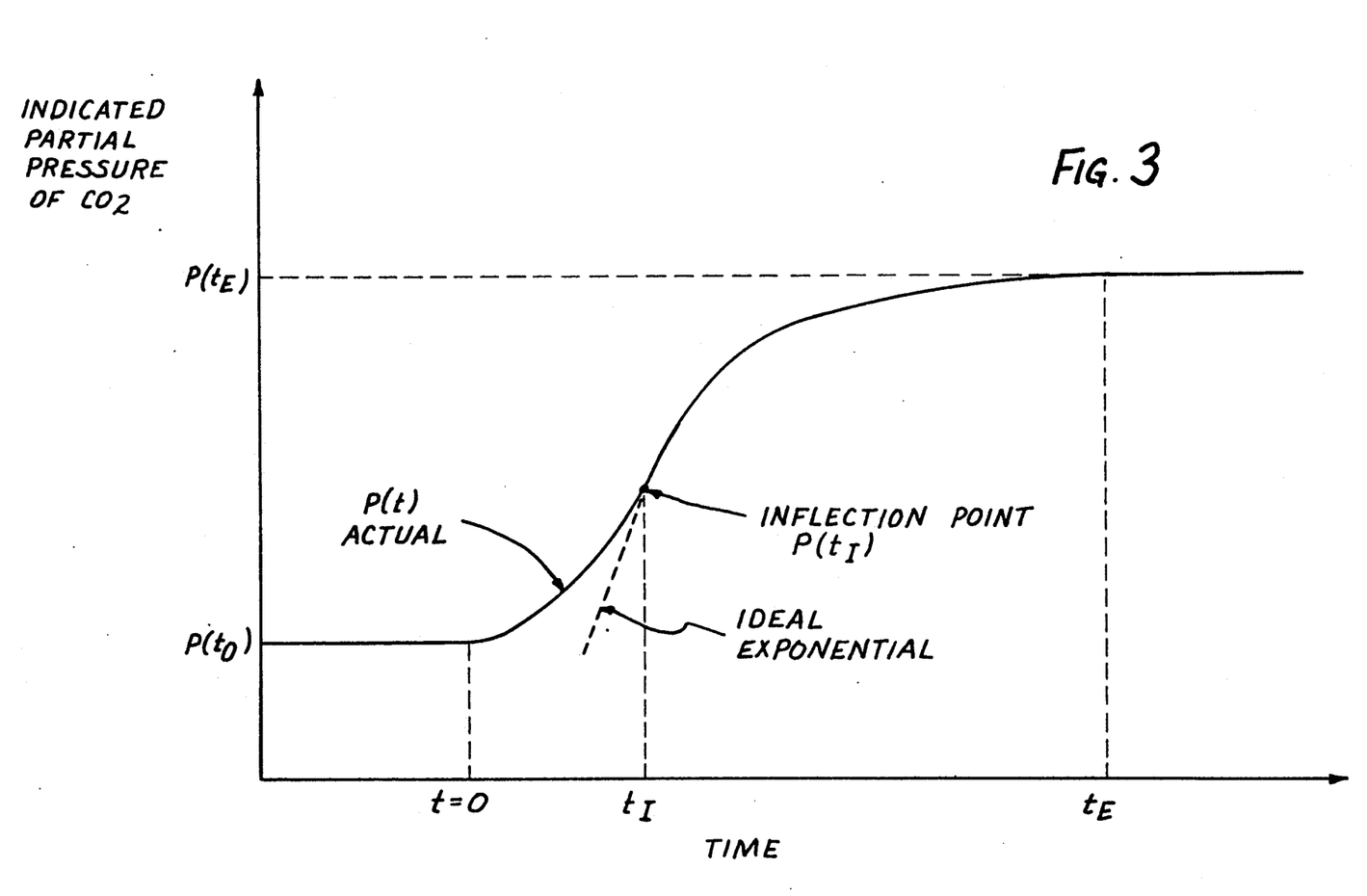
FIG. 3 is a plot of the partial pressure of carbon dioxide indicated by the sensor output versus time.

FIG. 3 represents a plot of the waveform $P(t)$ for a fluorescent sensor 18 which is responsive to the partial pressure of carbon dioxide ($CO_2$) The point on the abscissa designated $t=0$ is the point in time of the draw (i.e., the point in time at which blood is drawn into the housing portion 17). The initial value $P(t_0)$ on the ordinate is related to the partial pressure of $CO_2$ that is initially indicated before the draw (i.e., that of the flush solution) and the point equilibrated value $P(t_E)$ is related to the partial pressure of $CO_2$ finally indicated after equilibration (i.e., that of the blood sample).

The problem is that the waveform $P(t)$ varies from the initial indicated value $P(t_0)$ (e.g., 0.3 mmHg) to an asymptotic or equilibrated value $P(t_E)$ (e.g., 40 mmHg) along a path designated "P(t) ACTUAL" in FIG. 3 that is non-exponential. The P(t) actual curve deviates substantially from an ideal exponential curve (designated "IDEAL EXPONENTIAL") until it reaches the inflection point at $t_I$, after which it approximates the "ideal exponential." If the path were an ideal exponential curve, the coordinates of two points on that path would provide sufficient information to determine the equilibrated value $P(t_E)$. But that is not the case for the waveform $P(t)$ for $CO_2$. Nor is it the case for oxygen (FIG. 4) or for the pH value (FIG. 5).

Figure 4:
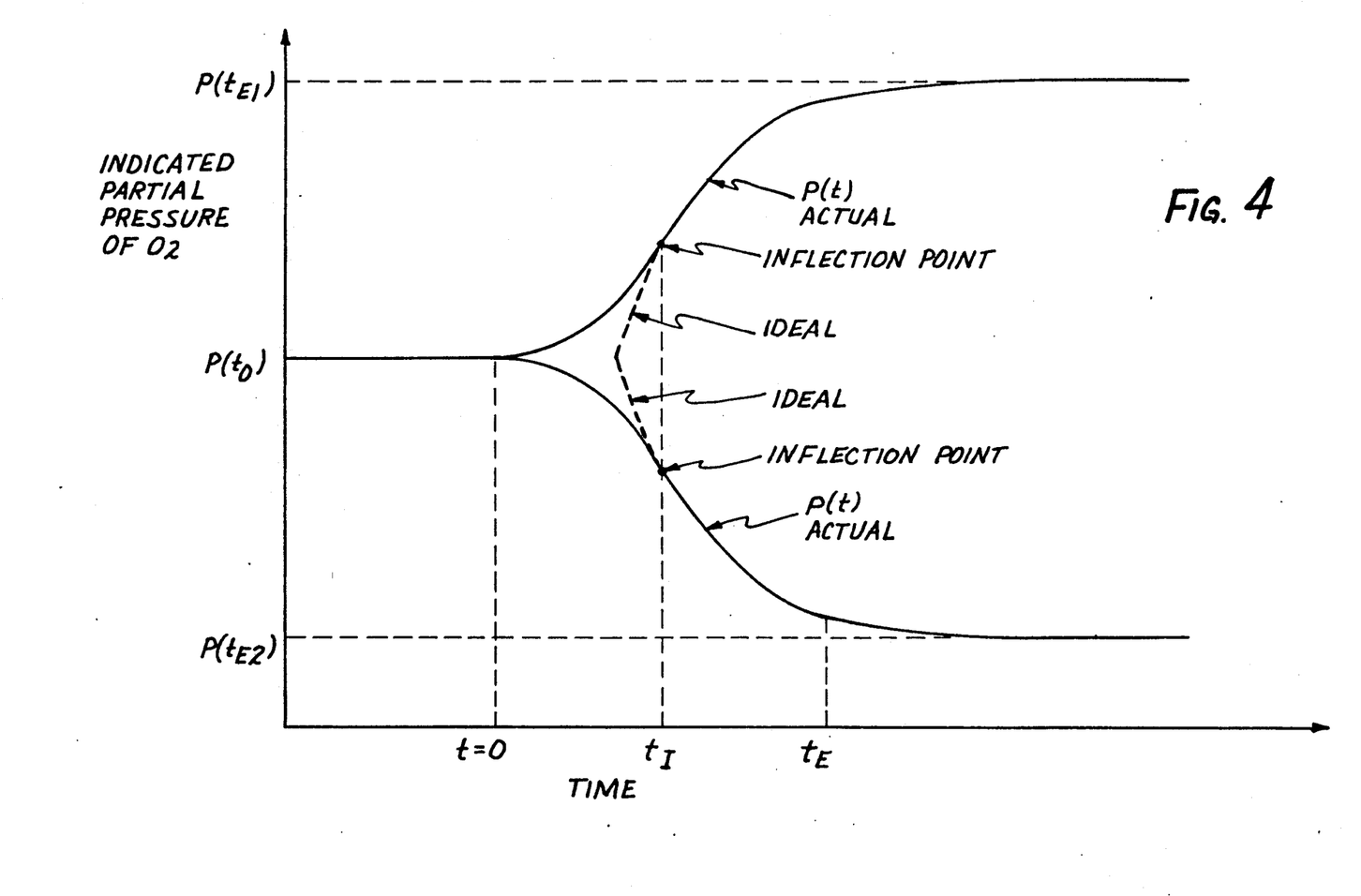
FIG. 4 is a representation of two plots of the indicated partial pressure of oxygen versus time.

In that regard, the upper plot in FIG. 4 represents a plot of the waveform $P(t)$ in the case of the sensor assembly 14 being responsive to the partial pressure of oxygen ($O_2$) in the blood sample. In that case, $P(t)$ varies from an initial value $P(t_0)$ (e.g., 150 mmHg for air to an equilibrated value $P(t_{E1})$ that is more (e.g., 220 mmHg for a patient taking oxygen). The lower plot in FIG. 4 also represents a plot of the waveform $P(t)$ in the case of the sensor assembly 14 being responsive to the partial pressure of $O_2$ in the blood sample. In that case, $P(t)$ varies from the initial value $P(t_0)$ to an equilibrated value $P(t_{E2})$ that is less (e.g., 80 mmHg for a patient not taking oxygen). In either case, the actual path (labelled "P(t) ACTUAL") varies substantially from an ideal exponential curve (labelled "IDEAL") until it reaches the inflection point at $t_I$, after which it approximates the "ideal exponential."

Figure 5:
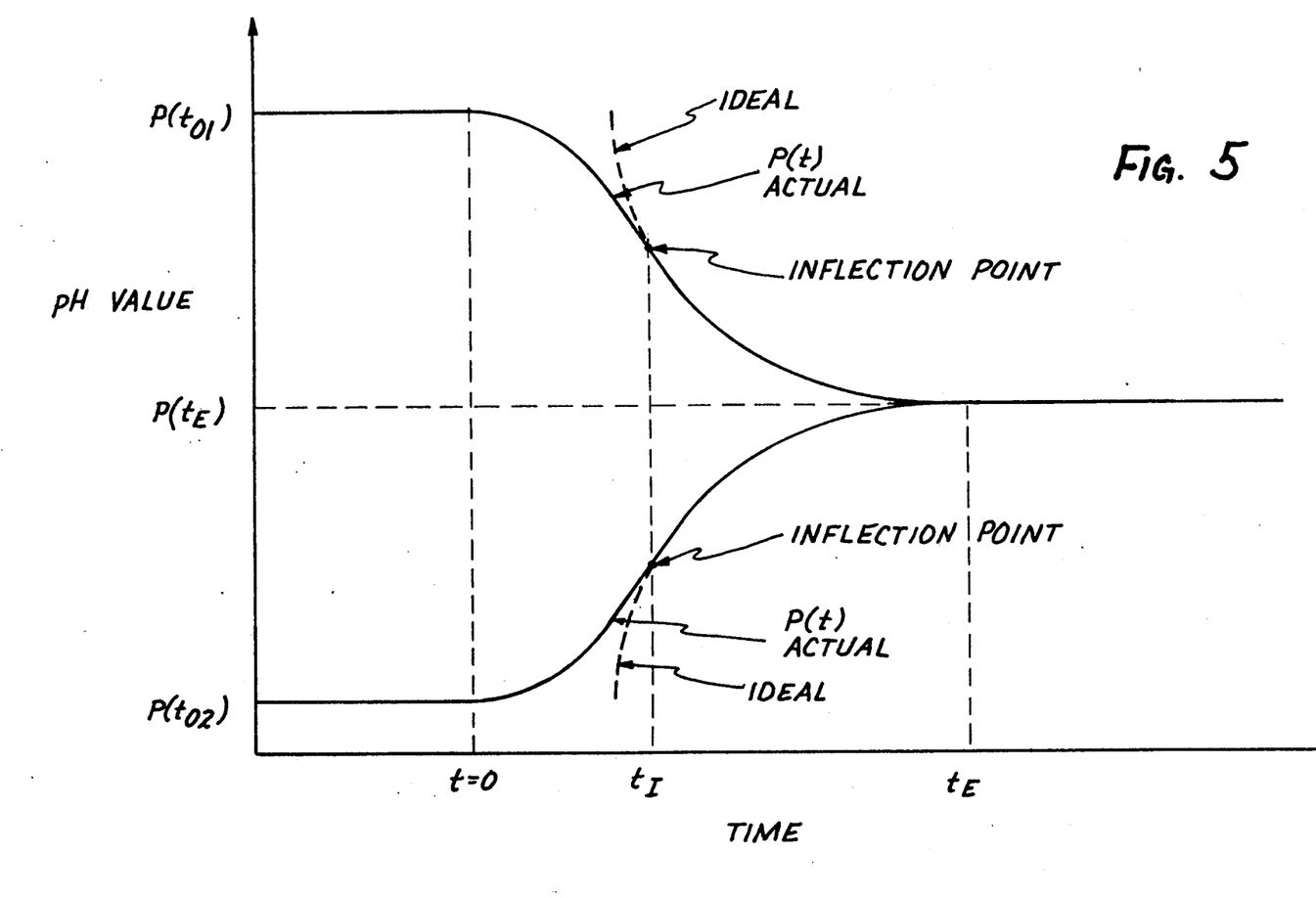
FIG. 5 is a representation of two plots of the pH value of blood versus time.

Similarly, both the upper and lower plots in FIG. 5 represent plots of the waveform $P(t)$ in the case of the sensor assembly 14 being responsive to the pH value of the blood sample. For the upper plot, $P(t)$ varies from an initial pH value $P(t_{01})$ that is above normal (e.g., suppose a pH of 8.5 for the flush solution) to an equilibrated value $P(t_E)$ (e.g., a pH of 7.4 for normal patient blood). For the lower plot, $P(t)$ varies from an initial pH value $P(t_{02})$ that is below normal (e.g., suppose a pH of 6.0 for some other flush solution) to the final indicated value $P(t_E)$ Once again, the actual path ("P(t) ACTUAL") varies substantially from an ideal exponential curve ("IDEAL") until it reaches the inflection point at $t_I$, after which it approximates the "ideal exponential."

Despite the deviation from a true exponential function, this invention predicts the equilibrated value by recognizing that $P(t)$ approximates a true exponential response after the occurrence of an inflection point $P(t_I)$. In other words, it varies exponentially from the inflection point $P(t_I)$ in that it at least approximates an exponential function of the type described by the relationship $$P(t) = A * (1 - \exp[-t/\text{Tau}]) + B$$

The inflection point, i.e., the point where the rate of change of the slope is zero, for each plot of $P(t)$ in FIGS. 3–5 is labelled "INFLECTION POINT" and each occurs at $t_1$ between $t=0$ and the time $t_E$ when the plot has substantially reached the equilibrated value (i.e., $P(t_E)$, $P(t_{E1})$, or $P(t_{E2})$, as the case may be). Using that characteristic, the present invention predicts the equilibrated value without requiring the estimation of the draw time and start time. Furthermore, the present invention does not require calculation of any time-consuming transcendental functions. Instead, the equilibrated value is predicted by calculating an estimated value using the current value of $P(t)$, the current measured slope, and an empirical estimate of Tau, the exponential response time. That calculation is repeated until the difference between subsequent iterations is sufficiently small.

In that regard, assume that a plot of $P(t)$ beyond the inflection point takes the form of an exponential function, so that $$P(t) = A * (1 - \exp\{-t/\text{Tau}\}) + B \quad (1)$$

where
B is an initial value,
A is the amount of exponential increase or decrease under certain conditions for $O_2$ and pH, and
$(A+B)$ is the asymptotic value.
Then, $$dp/dt = A * (1/\text{Tau}) * \exp[-t/\text{Tau}]$$

$$dp/dt = (A + B - P(t))/\text{Tau} \quad (2)$$

and $$(A+B) = P(t) + (\text{Tau} * dp/dt) \quad (3)$$

Thus, $(A+B)$ can be calculated using Equation (3) and an empirical estimation of Tau. According to one aspect of the invention, an estimated value of Tau for $CO_2$ is calculated using the relationship $$\text{TAU}_{est} = K_1 + K_2/\text{MAX}(dp/dt) \quad (4)$$

where $\text{TAU}_{est}$ is the estimated value of Tau, $K_1 = 15$, $K_2 = 5.5$, and $\text{MAX}(dp/dt)$ is the first derivative of $P(t)$ evaluated at the inflection point (i.e., the slope at the inflection point). That estimate is prompted by an analysis of certain sensor characteristics. First, generally any given sensor for determining the partial pressure of $CO_2$, $O_2$, pH or other compositional parameters responds more quickly or slowly to higher partial pressures, higher pH values or higher values of other compositional parameters. In the case of $CO_2$, Tau varies inversely with $(A+B)$. But, the present invention also recognizes that the first derivative or slope of $P(t)$ behaves somewhat consistently for most all sensors and most all partial pressures, pH values and values of other compositional parameters to the extent that there is an inflection point and that the waveform generally is exponential beyond the inflection point. That observation facilitates the prediction of the asymptotic or final indicated value of $P(t)$.

Tau is estimated according to one aspect of the invention by locating the inflection point $P(t_I)$ and then calculating an estimate of Tau using equation (4) above. Next, a new value of $(A+B)$ is calculated using equation (3). Then, the new value of $(A+B)$ is compared with the previous value and if the difference is sufficiently small (e.g., a change of less than one percent), that new value is taken as the asymptotic or final indicated value. Otherwise, another iteration is performed. Of course, the precise programming steps taken in determining $P(t_E)$ may vary within the broader inventive concepts disclosed so long as the determination is based upon the occurrence of the inflection point $P(t_I)$ and the exponential behavior of $P(t)$ thereafter.

The values of $K_1$ and $K_2$ given above were determined empirically according to another aspect of the invention after visual examination of various plots of $P(t)$ and $dp/dt$ for carbon dioxide indicated that the slope $dp/dt$ at the inflection point $P(t_I)$ was inversely related to the empirically observed Tau of each sensor, and this relationship was preserved over a wide range of equilibrated values $P(t_E)$.

More generally, Tau can be estimated using the relationship $$TAU_{est}K_1 + K_2 * \text{Max}(dp/dt)K^3 + K_4 * \text{MAX}(dp/pdt)^{K5} \quad (5)$$

where MAX(dp/dt) is the slope of $P(t)$ at the inflection point $P(t_1)$ and MAX(dp/pdt) is the maximum value of the proportional slope of $P(t)$ occurring near the inflection point $P(t_I)$, and $K_1$, $K_2$, $K_3$, $K_4$ and $K_5$ are constants. This equation can be used to estimate Tau for virtually any compositional parameter of blood. From the above equation, it can be seen that, for $CO_2$, $K_3 = -1$ and $K_4$ and $K_5 = 0$, thereby yielding equation 4 which is applicable to $CO_2$.

To determine the values of all of the "K" terms in equation 5, actual waveforms of pressure or pH versus time are plotted for the compositional parameter of interest over a wide range of equilibrated values $P(t_E)$, and from this set of waveforms, a least squares analysis is performed using equation 5 to determine the values of the "K" terms to best fit the set of waveforms.

Figure 6A:
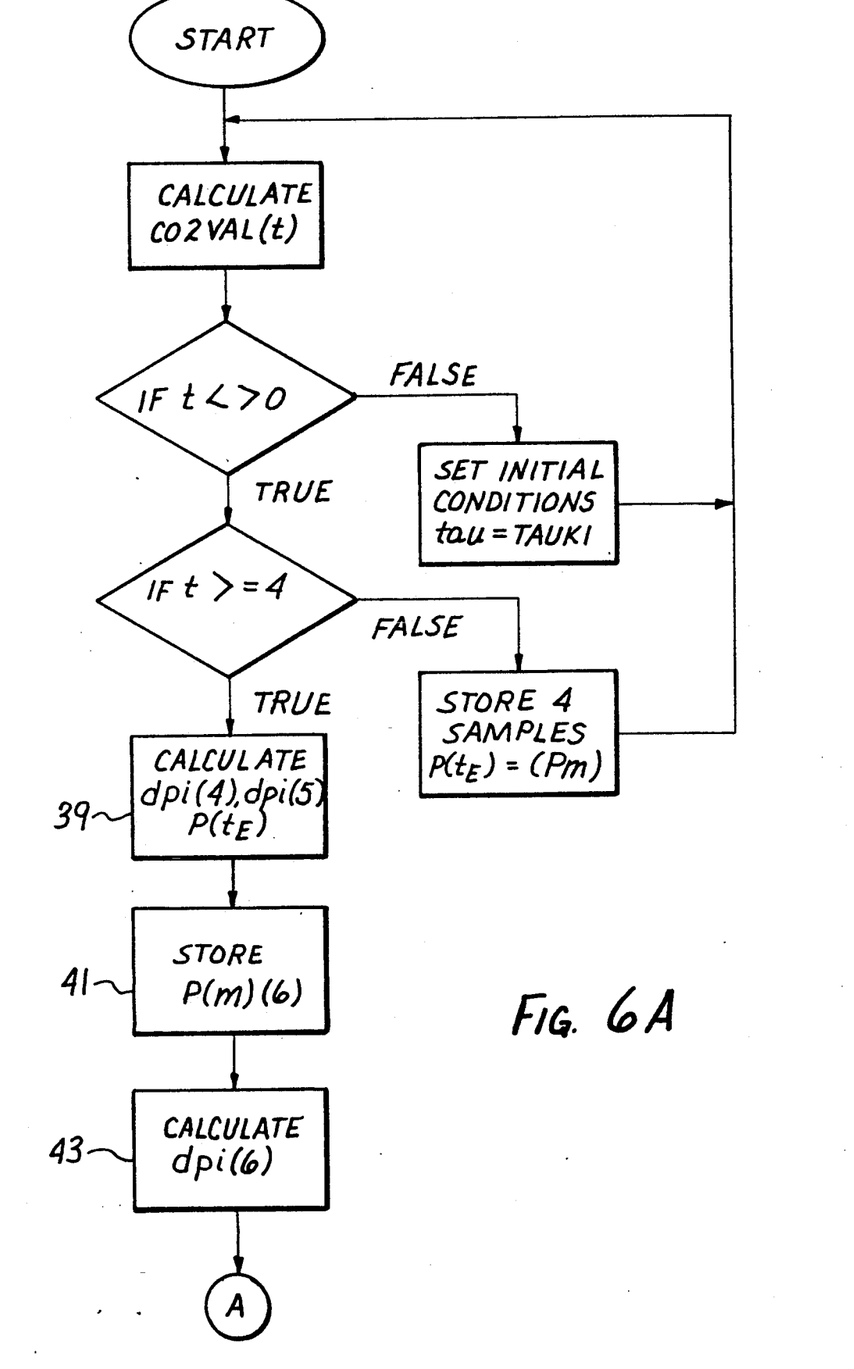
FIGS. 6A–6C combine as a flow chart a method for predicting equilibrated values.
Figure 6B:
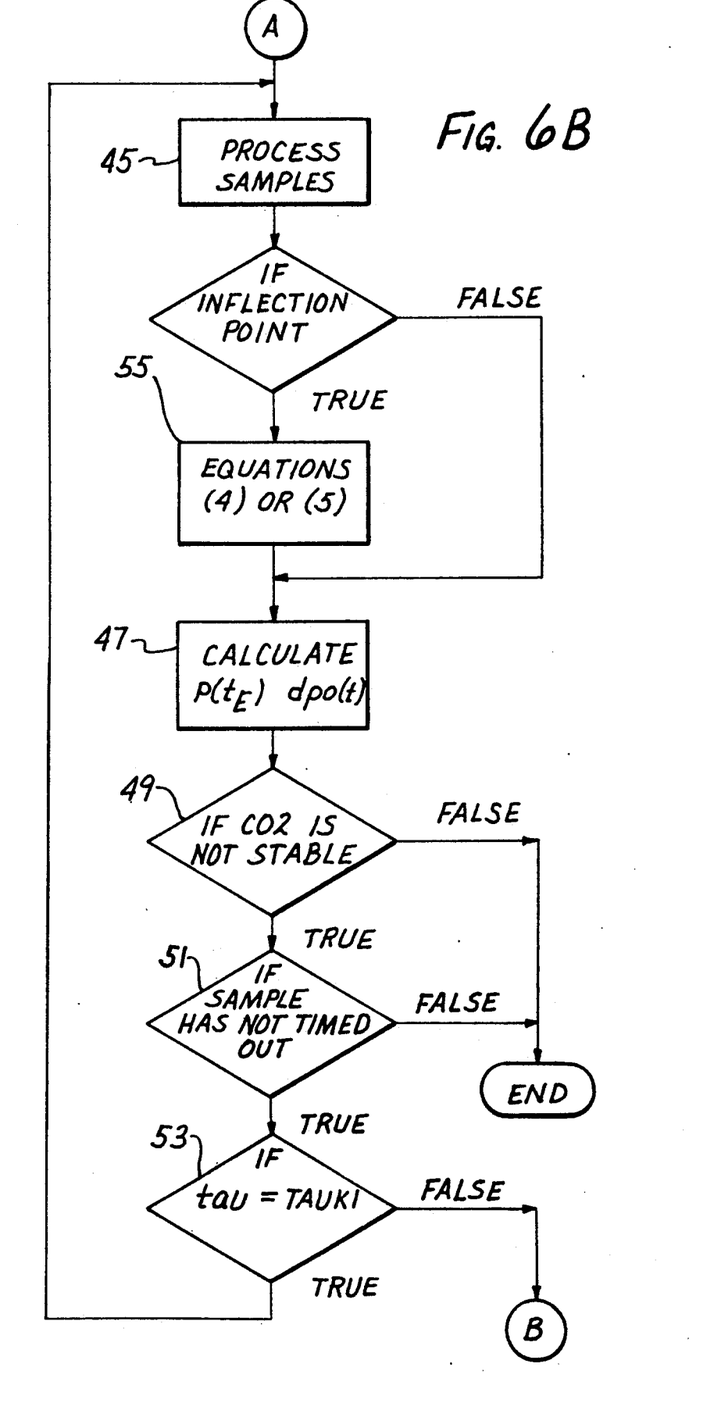
Figure 6C:
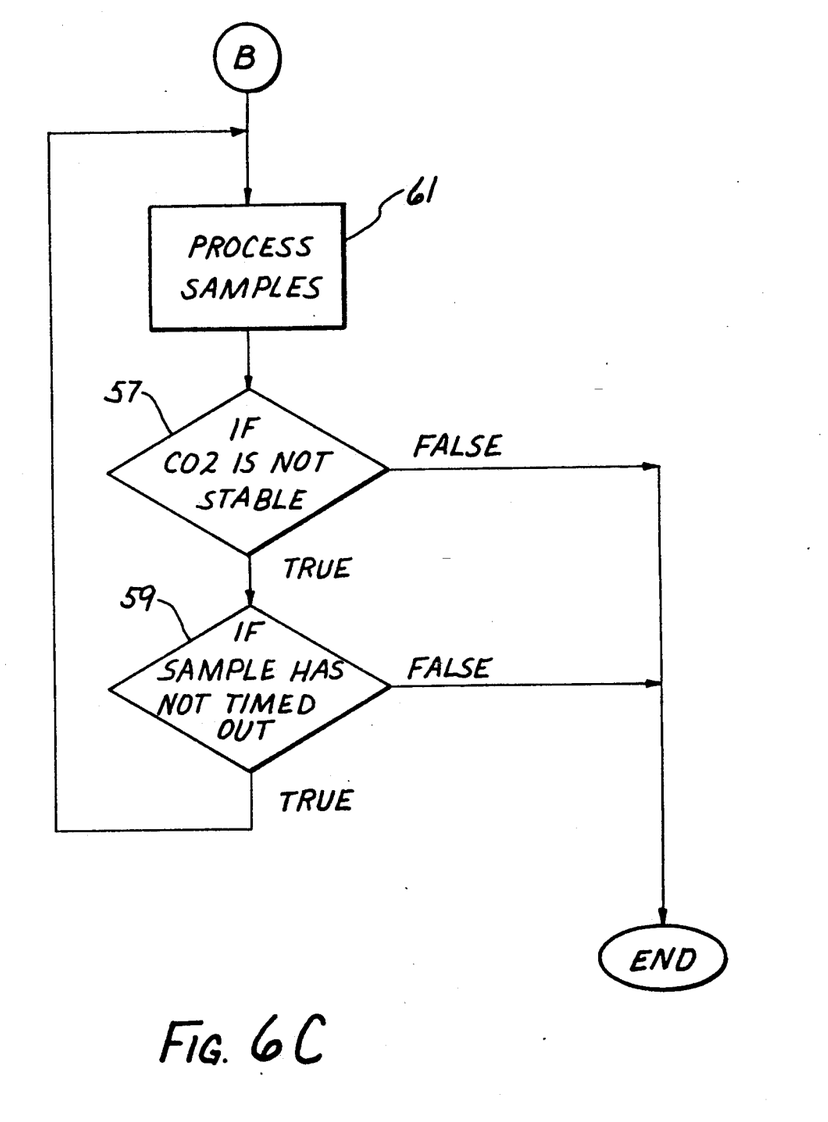

Considering now the flow chart of FIGS. 6A-6C, it shows the logical steps involved in predicting the equilibrated value $P(t_E)$ according to the prediction algorithm of the present invention. The prediction algorithm is integrated with other microprocessor programming used by the microprocessor circuitry 37. At START, blood is drawn into the housing portion 17, and the program sets initial conditions, which include the values or partial pressures of $CO_2$. If t is 0, the initial conditions Tau=TAUK$_1$ are set at 15 seconds, and the above steps repeated. If t, which represents the number of iterations or samples in the flow chart, is a value other than 0, then the first four values of $CO_2$ are displayed and stored, and the estimated final value of pressure, $P(t_E)$, is set equal to the measured values of pressure $P(m)$ for each of the measured values $P(m)$. After four samples are stored, initialization is complete. Next, the first derivative is calculated at block 39 using standard Savitzky-Golay polynomial filter methods and the $CO_2$ values or pressures for the fourth and fifth measured values of pressure. $P(t_E)$ is also calculated at block 39 using equation 3 and the fourth and fifth samples. Next the sixth $CO_2$ value is stored in a buffer at block 41 for future processing, and then the first derivative of the $P(t)$ curve is calculated at block 43 using the sixth sample and the Savitzky-Golay method.

At block 45 at the top of FIG. 6B, subsequently measured $CO_2$ values are processed in the same manner as at blocks 41 and 43, and the first derivative is continuously monitored. The monitoring of the first derivative is used to determine the inflection point by comparing the current first derivative against the previously calculated first derivative and identifying when the current derivative is less than the previous first derivative. When this occurs, the inflection point has been passed and is assumed to have occurred at the previous sample.

If the inflection point is not reached, $P(t_E)$ and dpo(t), which is the first derivative of $P(t_E)$, are calculated at block 47, and stability is determined at block 49. For example, stability may be determined by comparing the first derivatives of $P(t_E)$ for successive samples and identifying a measured $CO_2$ partial pressure to be stable if the variation in first derivatives of successive calculated $P(t_E)$ values is less than a predetermined amount. If the $CO_2$ value is not stable, then the process proceeds to a block 51 where a test is performed to determine if the sample has timed out. The sample has not timed out if a predetermined amount of time, such as two minutes, beginning with depressing of the start button has not elapsed.

In the pre-inflection period, i.e., prior to the time the inflection point is reached, block 53 is always true. Accordingly, the process described above in connection with FIG. 6B is repeated until the inflection point is reached. When the inflection point is reached, Tau is set at block 55 in accordance with equation 4 for $CO_2$ and in accordance with equation 5 for other compositional blood parameters. Because block 53 is now false, the process proceeds to block 57 in FIG. 6C to again determine if $CO_2$ is not stable. If this condition is false, then the calculated $CO_2$ value or partial pressure, $P(t_E)$, is stable and the proper final value has now been determined. However, so long as the estimated $CO_2$ value $P(t_E)$ is not stable, the process is subject to termination without determining a final partial pressure due to the sample time elapsing at box 59. Thus, assuming that the sample does not time out, the process shown in FIG. 6C repeats until the $CO_2$ values are determined to be stable, and that is taken as the estimated final value of, in the case of a blood gas, such as $CO_2$, partial pressure.

The blocks 49 and 51 in FIG. 6B represent safety features. Thus, if the condition $CO_2$ is not stable is false, i.e., $CO_2$ becomes stable before the inflection point is detected, or if the sample has timed out at block 51, the process terminates. In the case in which $CO_2$ is stable, the proper final value of the $CO_2$ value $P(t_E)$ has now been determined. In the case in which the sample times out, the most recently calculated value of $P(t_E)$ (calculated in block 47) is utilized as a rough estimate. The block 49 may be false, for example, if the start button is depressed too long a time following drawing of blood into the housing portion 17. The calculations of the block 47 (FIG. 6B) are repeated at the block 61 to repeatedly test whether the $CO_2$ values are determined as stable.

The blocks 51 and 59 also provide an overall time limit that the sample can remain in the housing portion 17, and if that time is reached before the equilibrated value is determined, the sample is returned from the housing portion 17 to the patient. In any event, the sample is returned to the patient before timeout occurs or before the time $t_E$ whichever occurs first. Normally, the sample is returned to the patient at some time between the detection of the inflection point and the time $t_E$. Preferably, the sample is returned to the patient soon after the inflection point is detected.

Although an exemplary embodiment of the invention has been shown and described, many changes, modifications and substitutions may be made by one having ordinary skill in the art without necessarily departing from the spirit and scope of this invention.

We claim:

1. A system for determining the value of a compositional parameter of blood, comprising:

means for containing blood;

sensor means on the containing means for producing a signal related to the value of the compositional parameter of blood;

computer means coupled to the sensor means for analyzing the signal and producing an output representing the value of the compositional parameter of blood;

wherein there is a delayed response such that the signal has a time-varying waveform P(t) that deviates from an exponential function as it varies from an initial value $P(t_0)$ occurring at a time $t_0$ at which the sensor means is subjected to the blood toward an equilibrated value $P(t_E)$ occurring at a time $t_E$ thereafter; and wherein the computer means includes means for detecting the occurrence of an inflection point $P(t_I)$ occurring between the initial value $P(t_0)$ and the equilibrated value $P(t_E)$; and means for computing an estimate of the equilibrated value $P(t_E)$ based upon the assumption that the waveform P(t) varies exponentially from the inflection point $P(t_I)$ to the equilibrated value $P(t_E)$.

2. A system as defined in claim 1, wherein the compositional parameter of blood is a blood gas, the sensor means is responsive to such blood gas, and said signal is related to the partial pressure of such blood gas.

3. A system as defined in claim 2 wherein the sensor means includes a fluorescent sensor responsive to the blood gas.

4. A system as defined in claim 3, wherein the compositional parameter of blood is $CO_2$ and the fluorescent sensor is responsive to $CO_2$.

5. A system as defined in claim 1, wherein the compositional parameter of blood is carbon dioxide, the sensor means is responsive to carbon dioxide and said signal is related to the partial pressure of carbon dioxide.

6. A system as defined in claim 1, wherein the compositional parameter of blood is oxygen, the sensor means is responsive to oxygen, and said signal is related to the partial pressure of oxygen.

7. A system as defined in claim 1, wherein the compositional parameter of blood is pH, the sensor means is responsive to pH, and said signal is related to the pH value.

8. A system as recited in claim 1, wherein the means for computing an estimate of the equilibrated value $P(t_E)$ uses the relationship $$(A+B)_{est} = P(t_I) + [\text{Tau} * \text{MAX}(dp/dt)]$$

where $(A+B)_{est}$ is the estimate of the equilibrated value, Tau is a constant, and MAX(dp/dt) is the slope of P(t) at the inflection point $P(t_I)$.

9. A system as recited in claim 8, wherein the means for computing an estimate of the equilibrated value $P(t_E)$ includes means for computing an estimated value of Tau using the relationship $$TAU_{est} = K_1 + K_2/\text{MAX}(dp/dt)$$

where $TAU_{est}$ is the estimated value of Tau, $K_1$ is a first constant, $K_2$ is a second constant, and MAX(dp/dt) is the slope of P(t) at the inflection point $P(t_I)$.

10. A system as recited in claim 9, wherein the value of $K_1$ is approximately 15 and the value of $K_2$ is approximately 5.5.

11. A system as recited in claim 8, wherein the means for computing an estimate of the equilibrated value $P(t_E)$ includes means for computing an estimated value of TAU using the relationship $$TAU_{est} = K_1 + K_2 * \text{MAX}(dp/dt)^{K_3} + K_4 * \text{MAX}(dp/pdt)^{K_5}$$

where MAX (dp/dt) is the slope of P(t) at the inflection point $P(t_1)$ and MAX (dp/pdt) is the maximum value of the proportional slope of P(t) occurring near the inflection point $P(t_I)$, and $K_1$, $K_2$, $K_3$, $K_4$ and $K_5$ are constants.

12. A system for determining the value of a compositional parameter of blood comprising:

a sensor exposable to blood for providing a signal related to the compositional parameter of the blood, said signal varying non-exponentially until it reaches an inflection point and approximately exponentially after the inflection point to a final value;

means for detecting the inflection point; and means for estimating the final value based on the assumption that the signal varies approximately exponentially after the inflection point.

* * * * *